United States Patent
Wilson et al.

(10) Patent No.: US 12,367,577 B2
(45) Date of Patent: Jul. 22, 2025

(54) SYSTEM AND METHOD FOR REVIEWING CAPSULE IMAGES WITH DETECTED REGIONS OF INTEREST

(71) Applicant: CAPSOVISION, Inc., Saratoga, CA (US)

(72) Inventors: Gordon C. Wilson, San Francisco, CA (US); Chenyu Wu, Sunnyvale, CA (US)

(73) Assignee: CAPSOVISION, INC., Saratoga, CA (US)

( * ) Notice: Subject to any disclaimer, the term of this patent is extended or adjusted under 35 U.S.C. 154(b) by 141 days.

(21) Appl. No.: 18/116,777

(22) Filed: Mar. 2, 2023

(65) Prior Publication Data
US 2024/0296551 A1 Sep. 5, 2024

(51) Int. Cl.
*G06T 7/00* (2017.01)
*A61B 1/00* (2006.01)
(Continued)

(52) U.S. Cl.
CPC ...... *G06T 7/0012* (2013.01); *A61B 1/000094* (2022.02); *A61B 1/0005* (2013.01);
(Continued)

(58) Field of Classification Search
CPC .............. G06T 3/20; G06T 2210/12; G06T 2207/30028; G06T 3/16; G06T 3/60;
(Continued)

(56) References Cited

U.S. PATENT DOCUMENTS 7,817,354 B2  10/2010  Wilson
7,983,458 B2  7/2011   Wang et al.
(Continued)

OTHER PUBLICATIONS

Liu J, Wang B, Hu W, Sun P, Li J, Duan H, Si J. Global and local panoramic views for gastroscopy: an assisted method of gastroscopic lesion surveillance. IEEE Transactions on Biomedical Engineering. Apr. 20, 2015;62(9):2296-307.*
(Continued)

*Primary Examiner* — Phu K Nguyen
(74) *Attorney, Agent, or Firm* — Blairtech Solution LLC

(57) ABSTRACT

Systems and methods are provided for processing images captured by a capsule camera system. According to one method, a frame sequence comprises panoramic picture representative of a GI scene covering substantially a lateral 360-degree Field-of-View is received. CADe (computer-assisted detection) is applied to detect one or more target abnormalities in the frame sequence, where said applying the computer-assisted detection (CADe) results in one or more CADe frames and each CADe frame contains at least one detection area containing a detected abnormality or a false positive. Circle shift is applied laterally to a target CADe frame to shift a detection area to a lateral center or close to the lateral center of the target CADe frame. The
(Continued)

CADe frames comprising the target CADe frame are provided with the detection area shifted to the lateral center or close to the lateral center of the target CADe frame.

23 Claims, 7 Drawing Sheets

(51) Int. Cl.
*G06T 3/16* (2024.01)
*G06T 3/20* (2006.01)
*G06T 3/60* (2006.01)
*G06T 11/00* (2006.01)
*A61B 1/04* (2006.01)

(52) U.S. Cl.
CPC .......... *G06T 3/16* (2024.01); *G06T 3/20* (2013.01); *G06T 3/60* (2013.01); *G06T 11/00* (2013.01); *A61B 1/041* (2013.01); *G06T 2207/10068* (2013.01); *G06T 2207/30028* (2013.01); *G06T 2210/12* (2013.01); *G06T 2210/41* (2013.01)

(58) Field of Classification Search
CPC .......... G06T 7/0012; G06T 11/00; G06T 2207/10068; G06T 2210/41; A61B 1/041; A61B 1/0005; A61B 1/000094
USPC ............................................. 345/418
See application file for complete search history.

(56) References Cited

U.S. PATENT DOCUMENTS

| | | | |
|---|---|---|---|
| 8,150,124 B2 | 4/2012 | Wang et al. | |
| 8,773,500 B2 | 7/2014 | Wilson et al. | |
| 10,876,168 B2 * | 12/2020 | Zou | B03C 1/015 |
| 11,100,633 B2 * | 8/2021 | Ngo Dinh | A61B 1/000096 |
| 11,221,333 B2 * | 1/2022 | Thorne | G01N 33/57407 |
| 11,618,926 B2 * | 4/2023 | Goel | C12Q 1/6886 |
| | | | 435/6.14 |
| 2022/0098680 A1 * | 3/2022 | Wang-Renault | C12Q 1/6886 |
| 2024/0084400 A1 * | 3/2024 | Vilar Sanchez | C12Q 1/6886 |

OTHER PUBLICATIONS

Fu Z, Jin Z, Zhang C, He Z, Zha Z, Hu C, Gan T, Yan Q, Wang P, Ye X. The future of endoscopic navigation: a review of advanced endoscopic vision technology. IEEE Access. Mar. 10, 2021;9:41144-67.*

Horie Y, Yoshio T, Aoyama K, Yoshimizu S, Horiuchi Y, Ishiyama A, Hirasawa T, Tsuchida T, Ozawa T, Ishihara S, Kumagai Y. Diagnostic outcomes of esophageal cancer by artificial intelligence using convolutional neural networks. Gastrointestinal endoscopy. Jan. 1, 2019;89(1):25-32.*

Guo L, Xiao X, Wu C, Zeng X, Zhang Y, Du J, Bai S, Xie J, Zhang Z, Li Y, Wang X. Real-time automated diagnosis of precancerous lesions and early esophageal squamous cell carcinoma using a deep learning model (with videos). Gastrointestinal endoscopy. Jan. 1, 2020;91(1):41-51.*

Hirasawa et al, "Application of artificial intelligence using a convolutional neural network for detecting gastric cancer in endoscopic images," Gastric Cancer, vol. 21, No. 4, pp. 653-660, Jul. 2018.*

Zenteno O, Trinh DH, Treuillet S, Lucas Y, Bazin T, Lamarque D, Daul C. Optical biopsy mapping on endoscopic image mosaics with a marker-free probe. Computers in Biology and Medicine. Apr. 1, 2022;143:105234.*

Kim DT, Cheng CH, Liu DG, Liu KC, Huang SW, Tran ST. Performance Improvement for Two-Lens Panoramic Endoscopic System during Minimally Invasive Surgery. Journal of Healthcare Engineering. 2019;2019(1):2097284.*

Oliveira M, Araujo H. Towards Robust Homography Estimation for Forward-Motion Panorama for Multi-camera Wireless Capsule Endoscopy Videos. InInternational Joint Conference on Biomedical Engineering Systems and Technologies Feb. 16, 2023 (pp. 1-23). Cham: Springer Nature Switzerland.*

Miley D, Machado LB, Condo C, Jergens AE, Yoon KJ, Pandey S. Video capsule endoscopy and ingestible electronics: emerging trends in sensors, circuits, materials, telemetry, optics, and rapid reading software. Advanced Devices & Instrumentation. Nov. 10, 2021.*

* cited by examiner

SYSTEM AND METHOD FOR REVIEWING CAPSULE IMAGES WITH DETECTED REGIONS OF INTEREST

CROSS REFERENCE TO RELATED APPLICATIONS

The present invention is related to U.S. Pat. No. 7,817,354, issued on Oct. 19, 2010, U.S. Pat. No. 7,983,458, issued on Jul. 19, 2011, U.S. Pat. No. 8,150,124, issued on Apr. 3, 2012 and U.S. Pat. No. 8,773,500, issued on Jul. 8, 2014. These U.S. patents are hereby incorporated by reference in their entireties.

FIELD OF THE INVENTION

The present invention relates to displaying in-vivo images captured inside the human body. In particular, the present invention relates to techniques of displaying images for time-efficient and reliable diagnosis of possible abnormality.

BACKGROUND

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Endoscopes allow a physician control over the field of view and are well-accepted diagnostic tools. However, they do have a number of limitations, present risks to the patient, are invasive and uncomfortable for the patient, and their cost restricts their application as routine health-screening tools.

Because of the difficulty traversing a convoluted passage, endoscopes cannot reach the majority of the small intestine and special techniques and precautions, that add cost, are required to reach the entirety of the colon. Endoscopic risks include the possible perforation of the bodily organs traversed and complications arising from anesthesia. Moreover, a trade-off must be made between patient pain during the procedure and the health risks and post-procedural down time associated with anesthesia.

An alternative in vivo image sensor that addresses many of these problems is capsule endoscope. A camera is housed in a swallowable capsule, along with a radio transmitter for transmitting data, primarily comprising images recorded by the digital camera, to a base-station receiver or transceiver and data recorder outside the body. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule.

An autonomous capsule camera system with on-board data storage was disclosed in the U.S. Pat. No. 7,983,458, entitled "In Vivo Autonomous Camera with On-Board Data Storage or Digital Wireless Transmission in Regulatory Approved Band". This application describes a capsule system using on-board storage such as semiconductor nonvolatile archival memory to store captured images or using a radio or other wireless transmitter to transmit captured images to a receiver outside the human body. After the capsule passes from the body, it is retrieved and the images stored are transferred over a communication link to a computer workstation for storage and analysis. For capsule images either received through wireless transmission or retrieved from on-board storage, the images will have to be displayed and examined by diagnostician to identify potential anomalies.

Capsule cameras conventionally have cameras facing one or both ends but may instead have cameras that provide a sideview, potentially a panoramic view. A sideview is required in order to view the tissue surface properly. Conventional devices are not able to see such surfaces, since their FOV is substantially forward looking. It is important for a physician to see all areas of these organs, as polyps or other irregularities need to be thoroughly observed for an accurate diagnosis. Since conventional capsules are unable to see the hidden areas around the ridges, irregularities may be missed, and critical diagnoses of serious medical conditions may be flawed. An optical imaging system and method for producing panoramic images exhibiting a substantial field of view is disclosed in U.S. Pat. No. 7,817,354, issued on Oct. 19, 2010. In one embodiment, a four-sided reflective pyramid with folded centers of perspective and optical axes associated with four cameras is disclosed to capture a full 360° Field of view. A capsule camera configured to capture a panoramic image of an environment surrounding the camera is disclosed in U.S. Pat. No. 8,773,500, entitled "In vivo Image Capturing System Including Capsule Enclosing a Camera". The panoramic camera is configured with a longitudinal field of view (FOV) defined by a range of view angles relative to a longitudinal axis of the capsule and a latitudinal field of view defined by a panoramic range of azimuth angles about the longitudinal axis such that the camera can capture a panoramic image covering substantially a 360° latitudinal FOV.

Similar to the situation with a conventional forward looking capsule system, for side-view and panoramic view capsule systems with digital wireless transmission or on-board storage, the captured images will be played back for analysis and examination. During playback, the diagnostician looks to find lesions or other points of interest as quickly and efficiently as possible. The playback is at a controllable frame rate and may be increased to reduce viewing time. However, if the frame rate is increased too much, the gyrations of the field of view (FOV) will make the video stream difficult to follow. At whatever frame rate, image gyration demands more cognitive effort on the diagnostician's part to follow, resulting in viewer fatigue and increased chance of missing important information in the video.

The course of imaging a patient GI tract (e.g. esophagus, stomach, small intestine and/or colon) using an endoscope results in over tens of thousands of image frames, typically. Due to the large amount of image data to be examined and the cost associated with the diagnostician's time, it is desirable to develop techniques to reduce the diagnostician's viewing time without compromising the quality and reliability of the diagnostics. In recent years, Artificial Intelligence (AI) has gained great momentum as a tool in assisting human visual tasks such as identifying medical conditions from diagnostic images. By using AI in medical imaging, physicians can identify conditions much faster so as to reduce the viewing time. With the expedited view process, physicians can spend more time and/or pay more attention to images likely having conditions.

For the GI images, it will take substantial time for a medical professional to review. The images will require around 20 minutes to display if they are displayed as video at about 30 frames per second. It would be a great risk for a medical professional to examine the images displayed as a video without any tool to assist the examination. Accordingly, various techniques have been developed and used in the field to detect possible anomalies (e.g. polyps or bleeding) in the GI images. For example, AI-based polyp detection can be used to save significant time for the medical professional as reported in various articles. Therefore, the medical professional only needs to focus on the frames containing detected polyps. The number of AI-detected frames hopefully will a small number, such as no more than about 100, so that the medical professional will be able to make reliable diagnosis within a giving time frame (e.g. 15 minutes). The attention paid to each image will be reduced as the number increases, raising the risk that the medical professional will judge an AI image to be FP (False Positive) when it is TP (True Positive).

In this application, we disclose a technique for efficiently viewing medical images and/or improving accuracy of diagnosing possible anomalies.

SUMMARY OF THE INVENTION

The present invention provides an effective method and system for viewing an image sequence generated from a capsule camera system. According to one method, the frame sequence, is received wherein each frame of the frame sequence comprises a panoramic picture representative of a GI scene covering substantially a lateral 360-degree Field of view (FoV). CADe (computer-assisted detection) is applied to detect one or more target abnormalities in the frame sequence, wherein said applying the computer-assisted detection (CADe) results in one or more CADe frames and each CADe frame contains at least one detection area comprising a detected abnormality or a false positive. Circle shift laterally is applied to a target CADe frame to shift a detection area to a lateral center or close to the lateral center of the target CADe frame. The CADe frames comprising the target CADe frame with the detection area shifted to the lateral center or close to the lateral center of the target CADe frame are provided.

In one embodiment, the method further comprises displaying the CADe frames on a display device. In one embodiment, the detection area is highlighted. In another embodiment, the detection area is highlighted using a bounding box.

In one embodiment, when the target CADe frame comprises two or more detection areas, the detection area closest to the lateral center of the CADe frames is highlighted and remaining detection areas are not highlighted. In another embodiment, at least one additional CADe frame is generated for one of the remaining detection areas and displayed, and wherein said one of the remaining detection areas is highlighted and circularly shifted laterally to near a center of said at least one additional CADe frame and other detection areas are not highlighted.

In one embodiment, for at least two or more closely located detection areas, at least two of said two or more closely located detection areas are highlighted jointly. In another embodiment, said two or more detection areas are highlighted by using a single bounding box to encompass said two or more detection areas.

In one embodiment, when one real abnormality appears at least in part in two detection areas at two edges of one target CADe frame prior to the circle shift, the two detection areas are united into one single detection area after the circle shift and said single detection area is highlighted.

In one embodiment, the CADe frames are displayed as a CADe sequence separated from the frame sequence and when one CADe frame displayed in a display window on a display device is selected for further viewing, the display window is switched to display the frame sequence or another display window is used to display the frame sequence. In another embodiment, after the display window is switched to display the frame sequence or said another display window is used to display the frame sequence, a starting frame of the frame sequence corresponding to the target CADe frame is displayed. In another embodiment, the starting frame is initially displayed with lateral shifting by a same distance as the target CADe frame. In another embodiment, the starting frame is displayed without the lateral shifting after a period. In one embodiment, the detection area is not highlighted after the display window is switched to display the frame sequence.

In one embodiment, when the frame sequence is displayed as a video, intermediate frames between a first target CADe frame and a next target CADe frame are displayed at a slower frame rate if a detection area distance between the first target CADe frame and the next target CADe frame is larger.

In one embodiment, when the frame sequence is displayed as a video and at least one CADe frame with one detection area is displayed for a period τ and nearby non-CADe frames in the frame sequence are display for shorter periods. In another embodiment, when the target CADe frame contains more detection areas, the target CADe frame is displayed for a longer viewing time.

In one embodiment, when the frame sequence is displayed, multiple display windows or a larger display window is used to display multiple frames of the frame sequence simultaneously to reduce viewing time.

In one embodiment, the frame sequence is displayed as a video and the frame sequence comprises intermediate frames without detection areas (non-CADe) between a first target CADe frame shifted by a first shift amount and a second target CADe frame shifted by a second shift amount, the intermediate frames without detection areas are displayed with laterally and circularly shifting in increments corresponding to fractions of a difference between the first shift amount and the second shift amount to avoid large shift between any two frames from the first target CADe frame to the next target CADe frame. In one embodiment, the increments associated with said laterally and circularly shifting are substantially equal. In another embodiment, the increments associated with said laterally and circularly shifting increase and then decrease between the first target CADe frame and the second target CADe frame.

DETAILED DESCRIPTION OF THE INVENTION

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely representative of selected embodiments of the invention.

Reference throughout this specification to "one embodiment," "an embodiment," or similar language means that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, or operations are not shown or described in detail to avoid obscuring aspects of the invention.

The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

Figure 1:
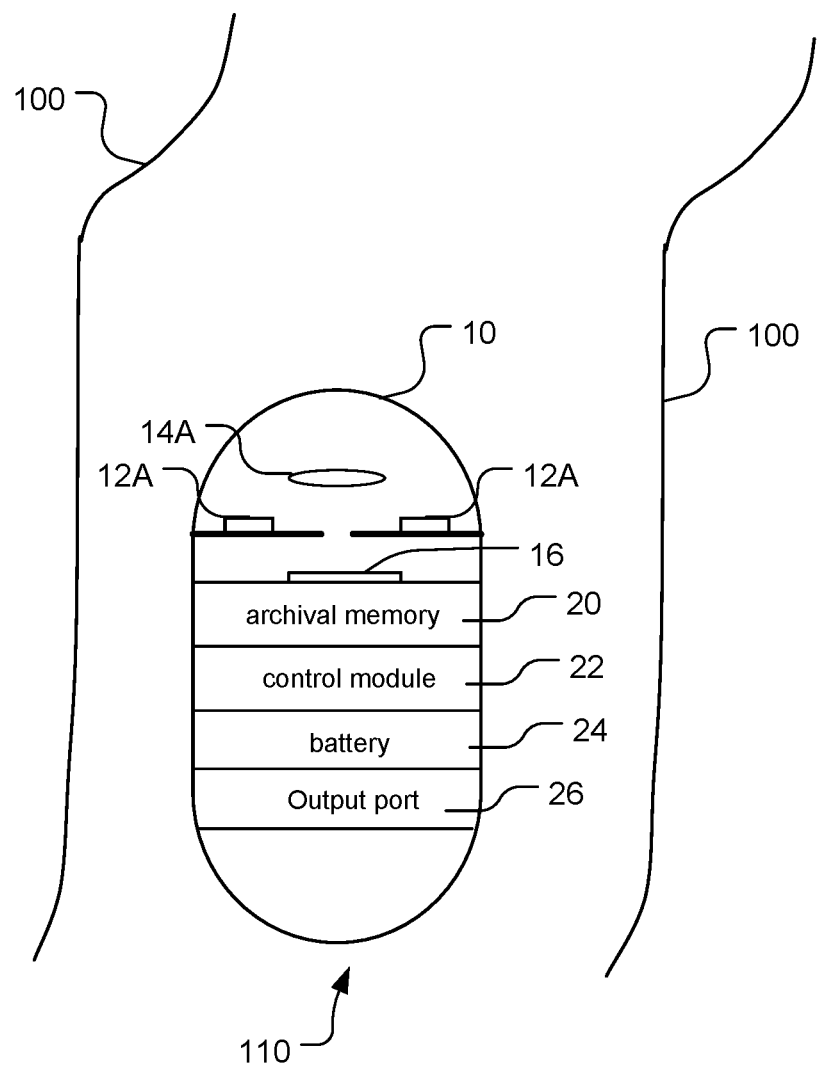
FIG. 1 shows schematically a capsule camera system in the GI tract, where archival memory is used to store capsule images to be analyzed and/or examined.

The present invention discloses methods and systems for improving the viewing process of diagnostic GI images so as to increase the efficiency and/or accuracy of examination by a diagnostician. The images may be received from a capsule camera system having on-board archival memory to store the images or received from a capsule camera having wireless transmission module. FIG. 1 shows a swallowable capsule system 110 inside body lumen 100, in accordance with one embodiment of the present invention. Lumen 100 may be, for example, the colon, small intestines, the esophagus, or the stomach. Capsule system 110 is entirely autonomous while inside the body, with all of its elements encapsulated in a capsule housing 10 that provides a moisture barrier, protecting the internal components from bodily fluids. Capsule housing 10 is transparent or at least transparent over the lens and LED areas, so as to allow light from the light-emitting diodes (LEDs) of illuminating system 12A to pass through the wall of capsule housing 10 to the lumen 100 walls, and to allow the scattered light from the lumen 100 walls to be collected and imaged within the capsule camera. Capsule housing 10 also protects lumen 100 from direct contact with foreign material inside capsule housing 10. Capsule housing 10 is provided a shape that enables it to be swallowed easily and later to pass through of the GI tract. Generally, capsule housing 10 is clean, made of biocompatible material, and is sufficiently smooth to minimize the chance of lodging within the lumen.

As shown in FIG. 1, capsule system 110 includes illuminating system 12A and a camera that includes optical system 14A and image sensor 16. A semiconductor nonvolatile archival memory 20 may be provided to allow the images to be stored and later retrieved at a docking station outside the body, after the capsule is recovered. System 110 includes battery power supply 24 and an output port 26. Capsule system 110 may be propelled through the GI tract by peristalsis. In the case of the capsule system using wireless transmission to send out the captured images, the archival memory 20 may not be used, instead the output port can be replaced by a radio or other wireless transmitter.

Illuminating system 12A may be implemented by LEDs. In FIG. 1, the LEDs are located adjacent to the camera's aperture, although other configurations are possible. The light source may also be provided, for example, behind the aperture. Other light sources, such as laser diodes, may also be used. Alternatively, white light sources or a combination of two or more narrow-wavelength-band sources may also be used. White LEDs are available that may include a blue LED or a violet LED, along with phosphorescent materials that are excited by the LED light to emit light at longer wavelengths. The portion of capsule housing 10 that allows light to pass through may be made from bio-compatible glass or polymer.

Optical system 14A, which may include multiple refractive, diffractive, or reflective lens elements, provides an image of the lumen walls on image sensor 16. Image sensor 16 may be provided by charged-coupled devices (CCD) or complementary metal-oxide-semiconductor (CMOS) type devices that convert the received light intensities into corresponding electrical signals. Image sensor 16 may have a monochromatic response or include a color filter array such that a color image may be captured (e.g. using the RGB or CYM representations). The analog signals from image sensor 16 are preferably converted into digital form to allow processing in digital form. Such conversion may be accomplished using an analog-to-digital (A/D) converter, which may be provided inside the sensor (as in the current case), or in another portion inside capsule housing 10. The A/D unit may be provided between image sensor 16 and the rest of the system. LEDs in illuminating system 12A are synchronized with the operations of image sensor 16. One function of control module 22 is to control the LEDs during image capture operation. The control module may also be responsible for other functions such as managing image capture and coordinating image retrieval.

After the capsule camera traveled through the GI tract and exits from the body, the capsule camera is retrieved and the images stored in the archival memory are read out through the output port. The received images are usually transferred to a base station for processing and for a diagnostician to examine. The accuracy as well as efficiency of diagnostics is most important. A diagnostician is expected to examine all images and correctly identify anatomical features, detect visualized abnormalities, and make a diagnosis. In order to help the diagnostician to perform the examination more efficiently without compromising the quality of examination, the received images are subject to processing to detect possible abnormalities visualized in the images. The detection process may be based on digital image processing techniques such as image classification, analysis, recognition, segmentation, etc. Recently, AI (in particular, the deep learning or convolutional neural network-based methods) has found great success in helping identifying targeted abnormalities (e.g. polyps) in medical images. The digital image processing techniques and the AI-based techniques for abnormality detection is often referred as a computer-assisted detection (CADe) technique.

Figure 2:
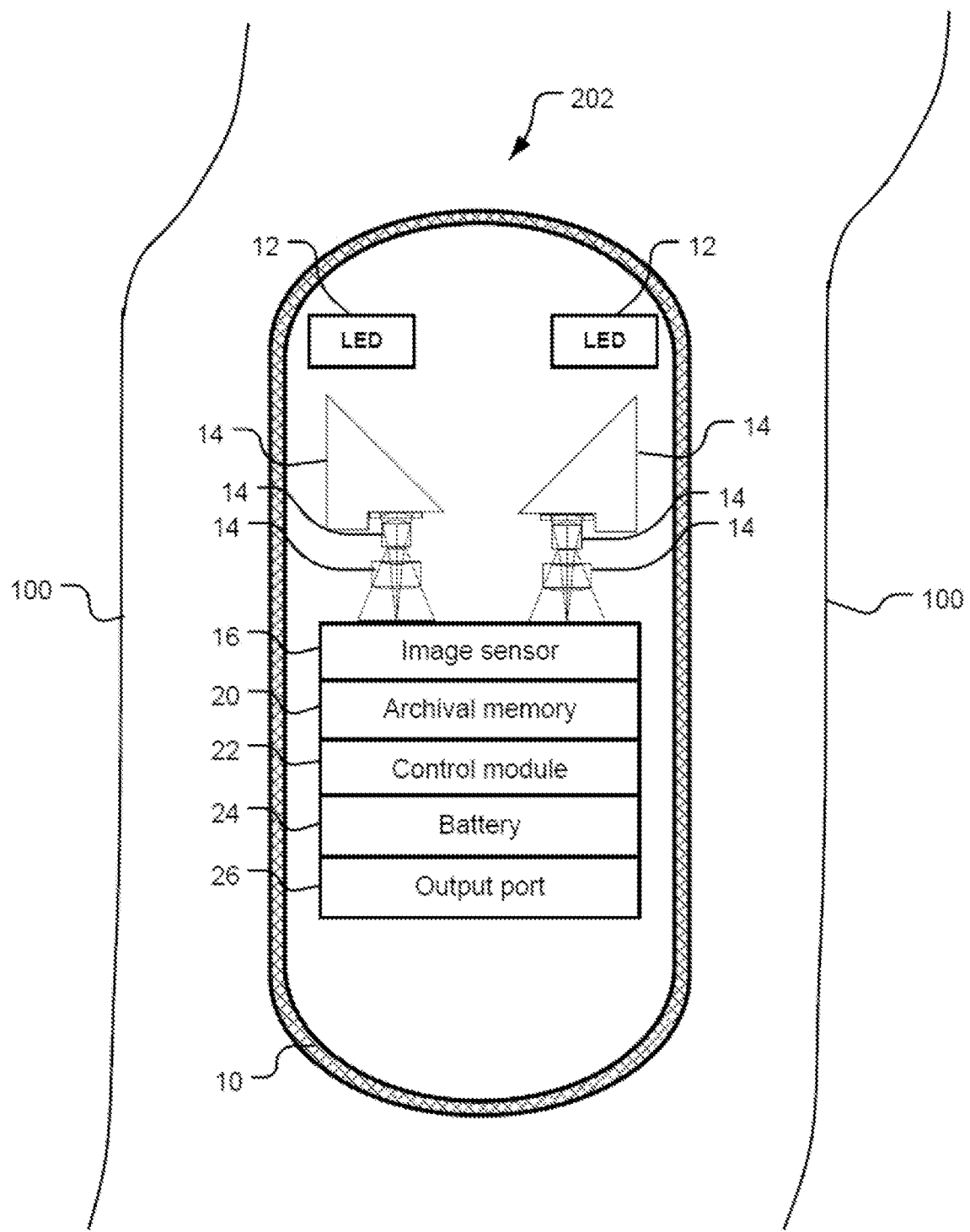
FIG. 2 shows schematically a panoramic capsule camera system in the GI tract, where archival memory is used to store capsule images to be analyzed and/or examined.

FIG. 2 shows an exemplary swallowable panoramic capsule system 202 inside body lumen 100. Lumen 100 may be, for example, the colon, small intestines, the esophagus, or the stomach. Panoramic capsule system 202 is entirely autonomous while inside the body, with all of its elements encapsulated in a capsule housing 10 that provides a moisture barrier, protecting the internal components from bodily fluids. Capsule housing 10 is transparent over the areas of lens and LEDs, to allow light from the light-emitting diodes (LEDs) of illuminating system 12 to pass through the wall of capsule housing 10 to the lumen 100 walls, and to allow the scattered light from the lumen 100 walls to be collected and imaged within the capsule.

As shown in FIG. 2, panoramic capsule system 202 includes illuminating system 12 and a camera that includes optical system 14 and image sensor 16. A semiconductor nonvolatile archival memory 20 may be provided to allow the images to be retrieved at a docking station outside the body, after the capsule is recovered. Panoramic capsule system 202 includes battery power supply 24 and an output port 26. Panoramic capsule system 202 may be propelled through the GI tract by peristalsis. Again, in the case of the capsule system using wireless transmission to send out the captured images, the archival memory 20 may not be used, instead the output port can be replaced by a radio or other wireless transmitter.

Illuminating system 12 may be implemented by LEDs. In FIG. 1, the LEDs are located adjacent to the camera's aperture, although other configurations are possible. The light source may also be provided, for example, behind the aperture. Other light sources, such as laser diodes, may also be used. Alternatively, white light sources or a combination of two or more narrow-wavelength-band sources may also be used. White LEDs are available that may include a blue LED or a violet LED, along with phosphorescent materials that are excited by the LED light to emit light at longer wavelengths. The portion of capsule housing 10 that allows light to pass through may be made from bio-compatible glass or polymer.

Optical system 14, which may include multiple refractive, diffractive, or reflective lens elements, provides an image of the lumen walls on image sensor 16. Image sensor 16 may be provided by charged-coupled devices (CCD) or complementary metal-oxide-semiconductor (CMOS) type devices that convert the received light intensities into corresponding electrical signals. Image sensor 16 may have a monochromatic response or include a color filter array such that a color image may be captured (e.g. using the RGB or CYM representations). The analog signals from image sensor 16 are preferably converted into digital form to allow processing in digital form. Such conversion may be accomplished using an analog-to-digital (A/D) converter, which may be provided inside the sensor (as in the current case), or in another portion inside capsule housing 10. The A/D unit may be provided between image sensor 16 and the rest of the system. LEDs in illuminating system 12 are synchronized with the operations of image sensor 16. One function of control module 22 is to control the LEDs during image capture operation.

The panoramic camera system shown in FIG. 2 is based on a system using a pyramidal reflective element having multiple reflective side facets facing in different directions. Each of the reflective side facets is associated with a component image in its respective direction. The panoramic camera system combines the component images to form a composite image. There are also other types of panoramic camera systems. For example, in U.S. Pat. No. 8,773,500, a panoramic camera system using a panoramic annular lens is described. The panoramic annular lens is configured to enable images to be captured by the panoramic camera radially about the longitudinal axis and onto the single image plane. The panoramic images captured by the system having panoramic annular lens reflective side facets represent continuous field of view up to 360°. On the other hand, the panoramic images captured by the system having a reflective element with multiple reflective side facets may represent multiple contiguous fields-of-view.

While the panoramic images may correspond to a 360° view of the lumen, a practical and convenient way to view the panoramic images is on an essentially flat display screen. Even when the display of choice has curvature, it usually is arced much less than 360°, the digital image is formatted for a rectilinear projection onto a flat display, and the display process may subsequently rectify the digital image data for display on a curved display instead of a flat display. Therefore, the panoramic image must be properly arranged in a pixelated digital representation for viewing on a flat screen. This formatting typically includes projection onto a virtual surface, such as a cylinder, which spans 360° and allows for the subsequent geometric transformations of cutting it and uncurling it onto a flat surface. In the description that follows, the projection object is a cylinder, but the cross-section of the cylinder need not be circular—it could be elliptical, irregular, or polygonal (i.e. the surface is a prism). The projection object surface could have curvature in the longitudinal direction, such as a sphere, or an ellipsoid, but projection onto a surface without longitudinal curvature, such as a plane, is then required. One or more cameras, each with a center of perspective (COP), and a field of view (FOV), captures an image of the scene. The images are projected from each camera's COP onto a virtual cylinder surrounding the cameras of a specified size and position relative to each camera. Projection is a well-known geometrical transformation that warps each image. If the cameras' FOVs overlap, then the projections onto the virtual cylinder overlap.

If the projection surface is cut longitudinally, it may be laid flat so that the composite image is mapped onto a plane. The location of the longitudinal cut line is arbitrary for a panorama and the image can be "circle shifted" by moving the cut line around the projection surface. Typically, the flat composite image is cropped to a rectangular frame. Also, the images from multiple cameras are typically stitched together to appear as a continuous image of the scene. Stitching involves registering the overlapping images and blending the images to minimize discontinuities, for example, in brightness and color. The magnification and distortion of each camera can be compensated to improve the registration of the images. If the centers of perspective are not coincident, then the view of an arbitrary scene from two cameras with overlapping FOVs will have parallax, which prevents a perfect registration of the images during the stitching process. The final panoramic image should appear continuous and omit little or no visualized scene representation, but some stitching artifacts may remain. Moreover, the final image may include warping steps to minimize stitching artifacts that are not strictly part of the projection described. While the final image ideally covers a 360° FOV completely, some small gaps may exist. Despite these imperfections, the composite image is still considered a panoramic image.

As an example, the panoramic image captured by the panoramic camera system with a 4-sided reflective element has 4 component images. Each component image corresponds to an image captured in a perspective direction and each component image may be slightly overlapped with its two neighboring component images. Each of four component images is projected onto a common virtual cylinder. A panoramic camera having a panoramic annular lens will provide continuous 360° field-of-view from a single camera so stitching is not required. In general, the panoramic image may be formed by a single image or by multiple overlapping images that are stitched together to form a single image.

Figure 3:
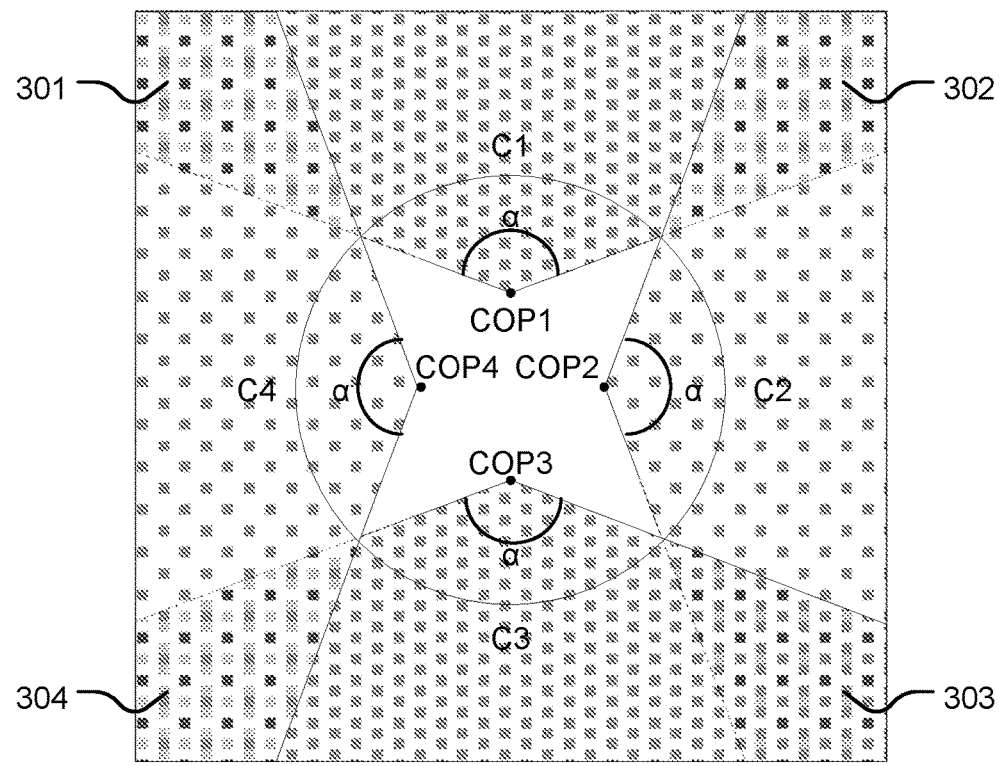
FIG. 3 illustrates an example of a panoramic imaging system with four cameras (C1, C2, C3 and C4), which are arranged to face 90•apart from neighboring cameras.

FIG. 3 illustrates an example of a panoramic imaging system with four cameras (C1, C2, C3 and C4 with COPs at COP1, COP2, COP3 and COP4 respectively), which are arranged to face 90° apart from neighboring cameras. Each camera covers a FOV covering an angle corresponding to α (α>90°) in the lateral direction. As shown in FIG. 3, the FOVs of two neighboring cameras are always overlapped as indicated by areas 301, 302, 303 and 304. When the camera COPs are not coincident with the center of the capsule housing, the FOV overlap increases with distance from the housing, and small regions of non-overlap on and near the outside surface of the housing may be acceptable in a panoramic image if the gaps in the 360° FOV are small (e.g. less than a few degrees of arc on the capsule surface). Gaps in the image scene will only occur where objects in the scene touch or come very close to the capsule and these gaps will be small (e.g. under 1 mm).

Figure 4A:
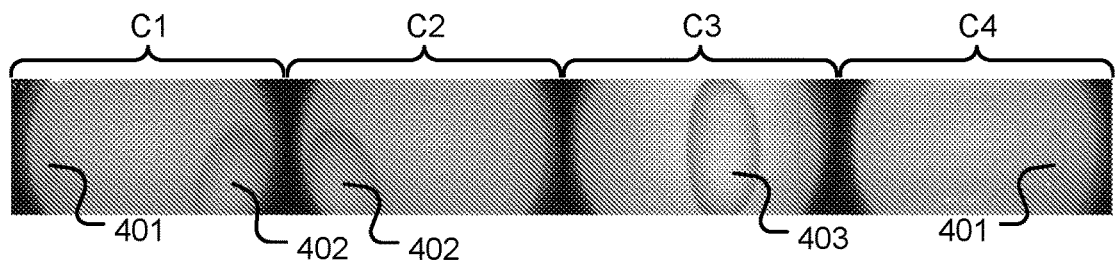
FIG. 4A illustrates an example of images captured by the four cameras under a test environment by placing objects within the FOVs of the cameras.
Figure 4B:
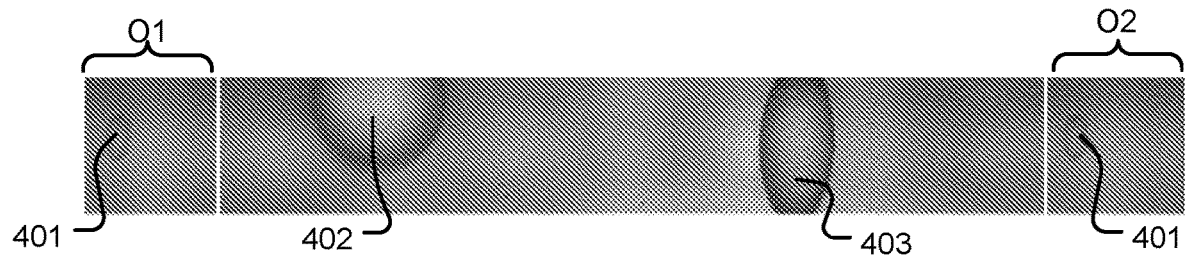
FIG. 4B illustrates an example of rectifying and stitching the four images from four cameras, as shown in FIG. 4A, into a single 360° panorama frame.

FIG. 4A illustrates an example of images captured by the four cameras under a test environment by placing objects (401, 402 and 403) within the FOVs of the cameras. As shown in FIG. 4A, some objects (401 and 402) may fall in the FOVs of two cameras. Accordingly, such objects will be captured by two cameras from different perspective angles (e.g. object 402 seen by cameras C1 and C2; object 401 seen by cameras C1 and C4). Furthermore, as shown in FIG. 4A, the images are substantially distorted due to the short distance between the objects and the camera lens. Therefore, the images need to be rectified to correct the distortion, and the rectification step can include projection onto a virtual object such as a cylindrical projection. For efficient viewing, these images from four cameras are preferred to be stitched into a single 360° panorama frame as shown in FIG. 4B. The images captured by individual cameras before stitching are referred to as component images in order to distinguish them from the stitched panoramic images (also referred as panoramas or frames in this disclosure).

Stitching eliminates the image redundancy where the fields-of-view overlap. The amount of overlap increases with the distance of objects from the capsule. The panorama wraps around and becomes shift invariant, since the panorama represent a 360° panoramic image. In one embodiment, some repeated areas (O1 and O2) near the edges are used in a frame as shown in FIG. 4B. Therefore, the same object (i.e., object 401) may appear in a frame twice. A panorama with wrap-around redundancy may be considered to display a scene arc exceeding 360° (e.g. 380°).

While the component images are stitched into frames to speed up the viewing process, there are still too many frames for a person to review in order to identify abnormalities in the frames captured during an examination. Accordingly, computer-assisted detection (CADe) is used in the present invention to reduce the burden on the reviewing clinician. Currently, there are various known techniques in the field for CADe, in particular, the deep-learning-based AI techniques, that can be used for abnormality detection, where the AI is trained on a set of images to detect particular feature classifications, which could include normal anatomical features but in this application are primarily targeted at abnormalities such as polyps and other lesions of the GI mucosa. CADe output facilitates patient diagnosis by the clinician.

In a typical capsule colonoscopy session, the frames that contain possible abnormalities represent a small percentage of the total frames. With the help of CADe, the effort of examining the frames can be substantially reduced. However, the frames without any detected abnormality cannot be ignored since the CADe is not perfect and may not detect an abnormality in all of the frames where it is present and it may miss some abnormalities completely. Viewing a video of the totality of frames showing an abnormality further facilitates diagnosis beyond the initial viewing of a subset of the abnormal frames. The frames containing detected target abnormalities are referred as abnormality-detected frames or CADe frames in this disclosure, and the frames without detected target abnormalities are referred as non-abnormality-detected frames or non-CADe frames. A region of a CADe frame containing the visualized abnormality (in whole or in part) is referred to as a detection area. The detection may correctly identify an abnormality (true positive) or incorrectly identify an abnormality (false positive). The terms "detection" and "detection area" apply in either case. The disclosure refers to particular abnormalities such as lesions or polyps, but the disclosure is not limited to these target abnormalities.

It is desirable that the display/viewing system provides an easy and effective way to allow a medical professional to switch between viewing CADe frames and viewing the full video with both CADe- and non-CADe frames. In one embodiment, a common video-playback window is used for both the CADe video (i.e., the CADe frames) and the full video (i.e., the original video containing both CADe and non-CADe frames), and users can switch between the two quickly. Ideally, switching videos does not require opening and re-opening a file, so as to reduce the viewing time. A large amount of data, such as full video data from a group of patients, often is stored in a secondary storage media such as a hard drive or flash memory or a storage-area network. When an image sequence is selected for examination, at least a portion of it will be loaded into system memory for processing and display. Since the number of CADe frames might typically be approximately 1000 and 1000 frames with image compression occupies roughly 30 MB, the CADe frames can all be stored in RAM (random access memory). Reviewing the CADe frames with video playback is desirable because 1000 frames are too many to click or scroll through comfortably. Adjusting the playback speed of the CADe video should not affect the previously set playback speed of the non-CADe, and visa versa. For the playback of CADe frames, a typical speed is likely a frame rate of about 1 fps (frame per second), allowing sufficient time for the clinician to evaluate each. At this rate, 1000 images require 17 minutes to review, not accounting for time spent scrutinizing particular frames, switching to the full video, or annotating images. The total review time for 1000 CADe frames may be unacceptable. Thus, the frame count should be further reduced to the extent possible without sacrificing the per-polyp sensitivity and the review process should be streamlined.

Figure 5A:
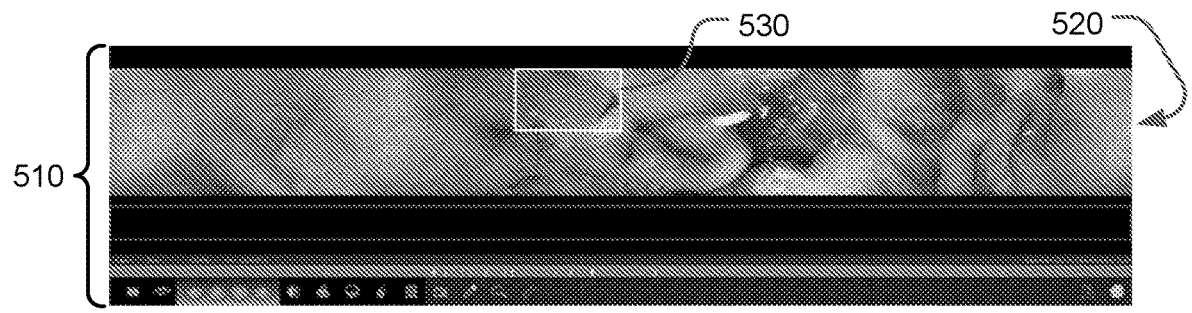
FIG. 5A and FIG. 5B illustrate an example of a display window shared by the CADe video and the regular video, where a frame of interest is found in the CADe frames (FIG. 5A), the user can switch to the regular video at the same frame (FIG. 5B) and navigate from there.
Figure 5B:
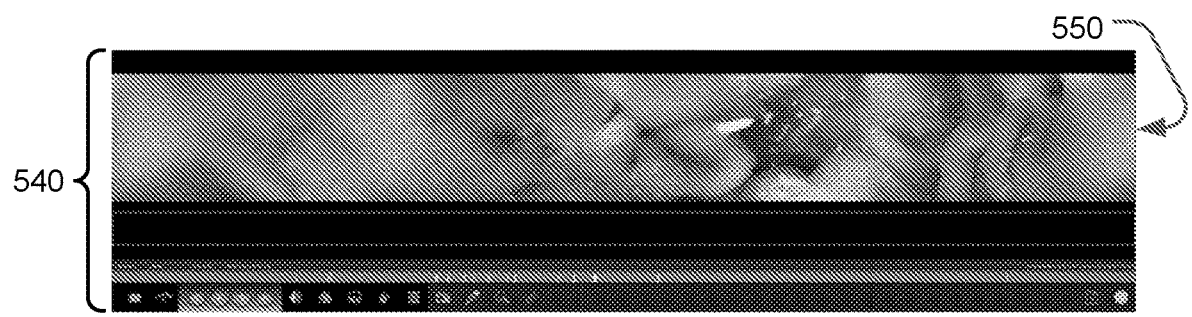

FIG. 5A and FIG. 5B illustrate an example of display window 510, shared by the CADe video and the regular video. When a frame of interest is found in the CADe frames (FIG. 5A), the user can switch to the regular video at the same frame (FIG. 5B) and navigate from there, potentially viewing nearby frames showing the abnormality, not all of which were CADe frames. In FIG. 5A, a CADe frame 520 is displayed with a detected abnormality highlighted by bounding box 530. A bounding box appears around the detected abnormality and is a common graphical way to highlight a detection area. A bounding box is illustrative in this application but other well-known methods of highlighting could be employed instead, such as bounding the detection area with a non-rectangular border, by modifying the color of pixels within the detection area, or by tagging or labeling the abnormality with a nearby graphical symbol, such as an arrow, or with nearby text.

According to an embodiment of the present invention, when a frame with a detection area is selected, the display window 540 is switched to a corresponding frame 550 in the regular video as shown in FIG. 5B. All polyp measurements and annotations could occur in the regular video. Upon returning to the CADe video, the current frame number would be the last-viewed CADe frame or the one after, so that the user can pick up where they left off with the CADe video review. However, since some of the remaining frames in the CADe video may now have been viewed in the full video, the UI (user interface) could mark these CADe frames so that the user knows that they have already been viewed. The UI could also include the option of skipping these frames or of automatically increasing the frame rate for displaying these images. The user can also use standard video navigation tools to scan through this portion of the CADe video more quickly.

It takes about ⅓ second to move the eyes' focus from one part of the frame to another, so tracking the bounding box as it jumps around from frame to frame adds about 5 minutes to the review time of 1000 images and fatigues the reader.

Since each frame is a 360° panorama, they can be circle-shifted so that the bounding box around the detection area is always in the center or close to the center of the frame laterally, i.e., the direction in which the image is panoramic. Typically, the lateral direction would be displayed horizontally, but it could be oriented in any direction. Circle shifting (or circular shifting) corresponds to a virtual rotation of the scene about the capsule. If the panoramic image initially covered scene azimuth about the capsule of 0° to 370° and a 90° circle shift is applied, the modified image displays 90° to 460° azimuths. As described earlier, circle shifting may also be considered a lateral translation of the longitudinal cut line on the projection surface. When the polyp is at the edge of the video frame, the polyp or portions of the polyp may appear in two neighboring cameras at the same time, as indicated by the two peripheral bounding boxes (e.g. 602 and 604 in FIG. 6A). In some cases, the polyp may not be visible in its entirety at either edge. Areas 610 and 612 indicate the overlapped areas on both edges in the horizontal direction. By circle shifting the panorama to move the detection area to the center, a single bounding box 622, which includes the target abnormality, can be presented in the center of the frame (FIG. 6B) and the polyp is visible in its entirety—or at least the entirety of the portion that has been captured by the camera(s) in this frame—facilitating its analysis. Areas 630 and 632 indicate the redundant wrap-around areas on both edges in the horizontal direction, which must be considered when graphically performing the circle shift. For a shift of n pixels to the right, the wraparound redundancy is increased by at least n pixel columns on the left. Then the expanded image is shifted to the right n pixels and cropped to fit the original frame. Similarly, a shift to the left involves increasing the wraparound on the right edge. Also, a shift of n columns to the left is equivalent to a right shift of Nc−n columns, where Nc is the total number of columns in the image (its width). The same result can be achieved by breaking up the operations into smaller steps and reordering them. For example, the cropping can be done first and either the left area 610 or the right area 612 can be removed so that the frame becomes a continuous picture of the scene that flows from the left edge into the right edge circularly. Alternatively, the left half of the left area 610 and the right half of the right area 612 can be removed so that the frame becomes a continuous picture that flows from the left edge into the right edge circularly. After the frame is circularly shifted in the horizontal direction to move the bounding box 622 to the center or close to the center, redundant wraparound pixel data is added to areas 630 and 632, as needed, to fill the frame, as shown in FIG. 6B.

Figure 6A:
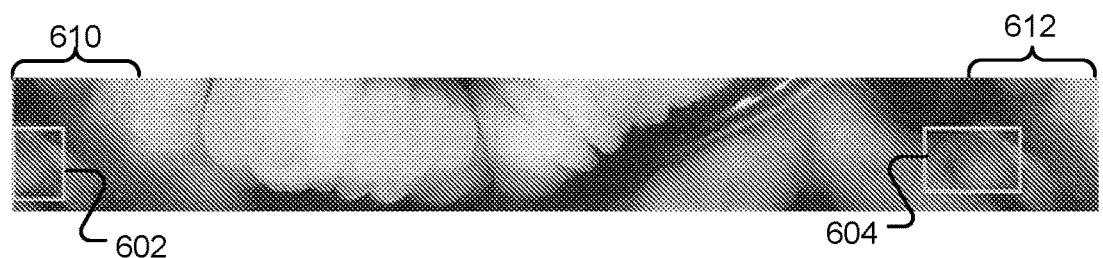
FIG. 6A illustrates an example that, when the polyp is at the edge of the video frame, two peripheral bounding boxes may appear.
Figure 6B:
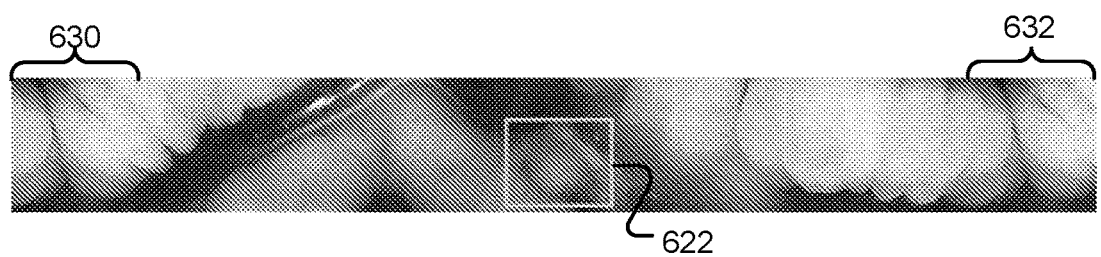
FIG. 6B illustrates an example to reunite two objects (as shown in FIG. 6A) seen at two edge of the frame into one object.
Figure 7:
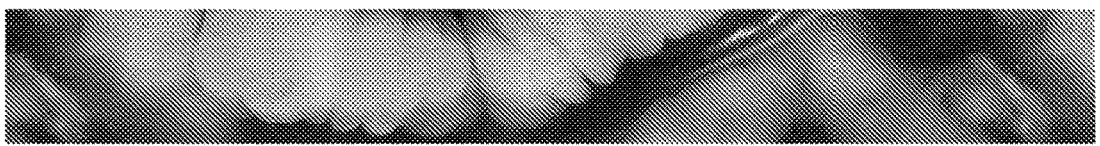
FIG. 7 illustrates an example of a frame in the frame sequence corresponding to the CADe frame in FIG. 6A.

If the user now switches to the full video, the display briefly shows the un-rotated (unshifted) image with the detection area(s) and corresponding bounding box(es) in their un-shifted position(s) (FIG. 6A) so that the user knows where to look for the un-highlighted detection area(s) in the main video (FIG. 7), where the frame in FIG. 7 is a frame in the main video corresponding to the CADe frame in FIG. 6A.

Figure 8A:
FIG. 8A illustrates an example of a CADe frame containing multiple independent detection areas covering non-overlapping image data.
Figure 8B:
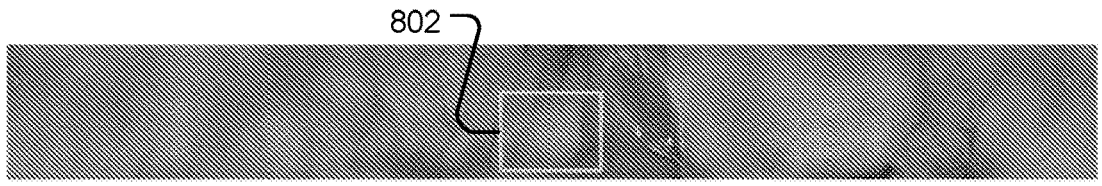
FIG. 8B illustrates an example of an additional CADe frame containing one of the two independent detection areas being generated.
Figure 8C:
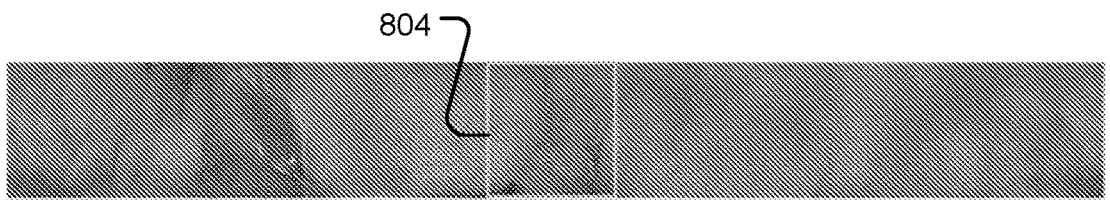
FIG. 8C illustrates an example of an additional CADe frame containing the other of the two independent detection areas being generated.

If the frame has multiple independent detection areas (802 and 804) covering non-overlapping image data (FIG. 8A), the same frame can be presented multiple times sequentially according to one embodiment, once for each distinct detection area, circle-shifted so that the detection areas are always in the center and the user's gaze does not need to be split over multiple bounding boxes. FIG. 8B illustrates the case that detection area 802 is shifted to the center and FIG. 8C illustrates the case that detection area 804 is shifted to the center. In another embodiment, when a CADe frame comprises two or more detection areas, the detection area closest to the lateral center of the CADe frames can be highlighted and remaining detection areas are not highlighted.

Figure 9A:
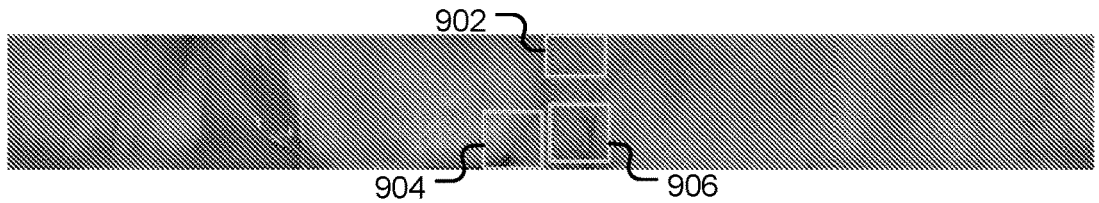
FIG. 9A illustrates an example of a CADe frame with three closely-located objects (as indicated by three bounding boxes).
Figure 9B:
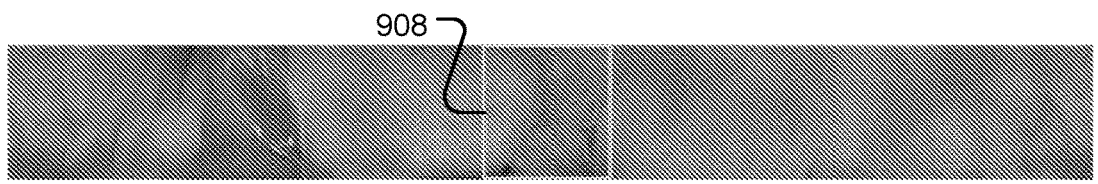
FIG. 9B illustrates an example that these three objects as shown in FIG. 9A are enclosed by a single bounding box.

In one embodiment, when multiple detection area bounding boxes are close together, they could be replaced by a single encompassing bounding box so that a viewer can focus on all these abnormalities at once. Sometimes the CADe may identify portions of a single abnormality, such as a lesion, as separate detection areas matching the target classification ("abnormal") with the interstitial pixels misclassified as "normal," in which case, a single encompassing bounding box is a more accurate and less distracting highlighting of the abnormality than multiple boxes. FIG. 9A illustrates an example with three closely-located detection areas (as indicated by three bounding boxes 902, 904 and 906). According to one embodiment, these three detection areas can be highlighted jointly. For example, these detection areas can be enclosed by a single bounding box 908 as shown in FIG. 9B, creating a single larger detection area. The same process can be applied with other types of detection-area highlighting besides bounding boxes.

Since each frame is a panorama of approximately 360° or greater, moving across the frame from 0° to 360° and then wrapping around to 0° again is described by a periodic function. The lateral circle shift can be considered a phase shift of the periodic function, corresponding to scene rotation. The phase can be shifted so that the detection area is in the center without cropping unique image data. If fewer pixels than the frame width are needed to cover 360°, after stitching images to form the panorama, image data may be duplicated at the edges to fill the frame. When the image scene is rotated, the image data that is duplicated will now be data that has moved to an edge.

Figure 10:
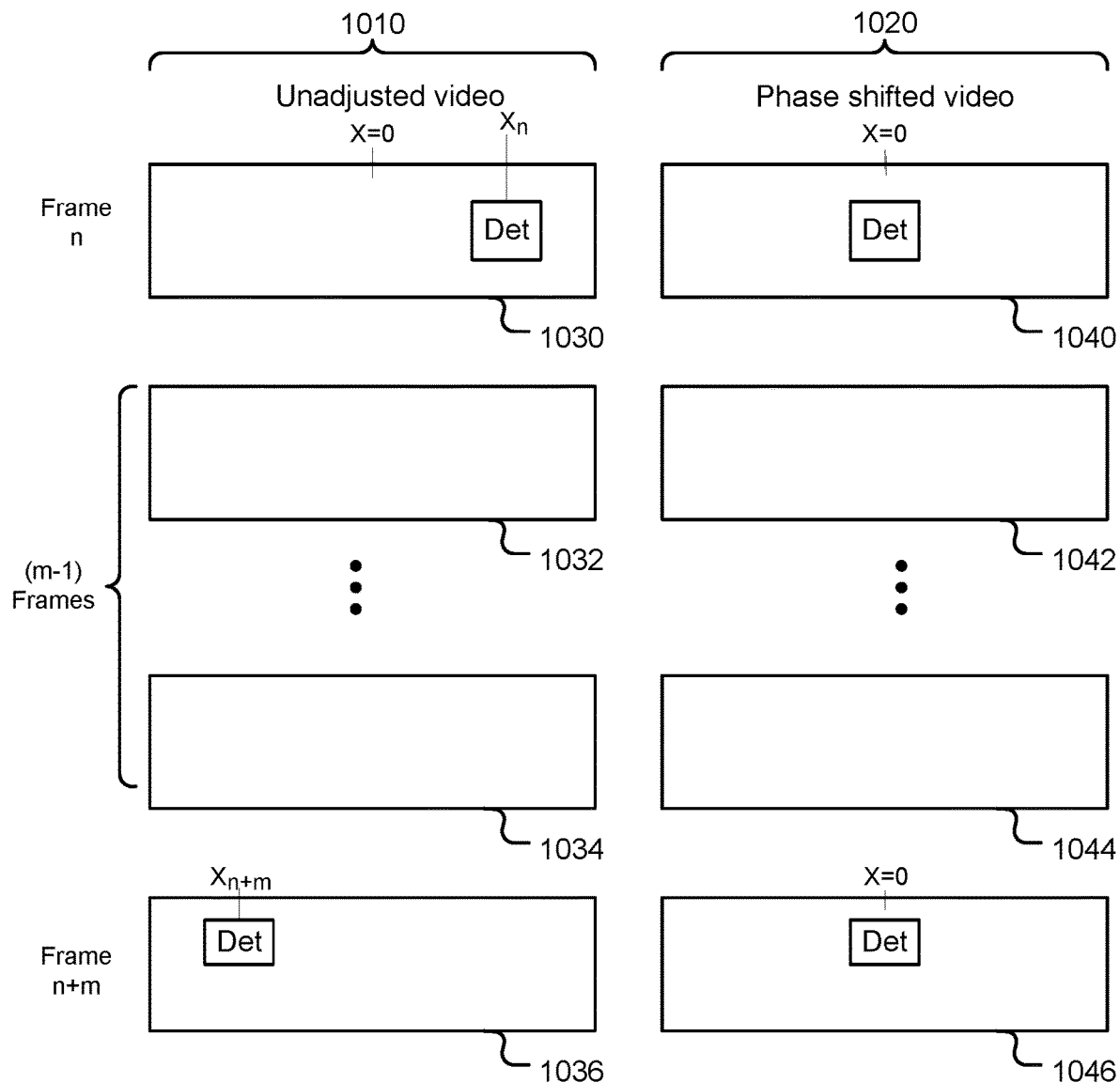
FIG. 10 illustrates an example of an incremental phase shift to the frames without detection areas between two frames with detection areas to prevent rapid rotations of the scene.

As mentioned earlier, when a frame containing a detection area is viewed in the CADe video, the viewer may decide to switch to the full video for detailed viewing, according to one embodiment. For example, while viewing the CADe frames, the reviewer may decide to select one CADe frame for further viewing. In this case, the display window is switched to display the frame sequence. In one embodiment, after the display window is switched to display the frame sequence, a starting frame of the frame sequence corresponding to the CADe switched-from frame is displayed. The switch may be triggered using an input device such as a computer mouse, a keyboard, a key pad, or one or more buttons. Furthermore, according to another embodiment, a switched-to frame in the full video is displayed with the same phase shift as the corresponding switched-from frame in the CADe-only video. There may be non-CADe frames in the full video between two CADe frames. A viewer may experience rapid rotation of the scene transitioning from a shifted frame to a non-shifted frame. To prevent rapid rotations of the scene, an incremental phase shift to those frames without detection areas between two frames with detection areas is disclosed as shown in FIG. 10. The increment could be the total phase shift evenly divided by m, the number of frames from one detection-area frame to the next in one embodiment. For example, a current frame containing a detection area corresponds to frame n 1030 in the full video without shifting and the next CADe frame corresponds to frame (n+m) 1036 in the full video without shifting. The horizontal location of the detection area (Det.) in frame n is $x_n$ and horizontal location of the detection area (Det.) in frame (n+m) is $x_{n+m}$. There are (m−1) frames (from 1032 to 1034) in between without any detection area. On the right-hand side, the shifted full video is shown. Frame 1040 corresponds to frame n with the detection area shifted to the center. Similarly, frame 1046 corresponds to frame (n+m) with the detection area shifted to the center. The total shift distance to be performed between frame n and frame (n+m) is $(x_n-x_{n+m})$. Therefore, each frame should be shifted by $(x_n-x_{n+m})/m$ from the previous frame. Such uniform shifting will result in a smooth transition from one frame with the detection area to the next one with the detection area. In one embodiment, the detection areas in the CADe frames in the full video are highlighted, for example by bounding boxes, in which case the CADe-only video is not necessarily viewable. In another embodiment, the detection areas are not highlighted in the full video and the reviewer must switch to a CADe-only video to observe the detection area highlighting. In either case, it may be possible for the user to toggle the detection area highlighting on and off using the interfaces of the UI.

According to another embodiment of the present invention, as the full video is played, the display control will automatically slow down the video for CADe frames. Each single-detection-area CADe frame could be displayed for a fixed time τ deemed adequate to evaluate the detection area. The viewer can always pause the video to spend even more time on the frame. The review time is decreased by viewing the non-CADe frames relatively rapidly. Preferably in this embodiment, the detection areas are highlighted when viewing the full video. They may be toggled on and off in a particular frame after pausing the video to enable inspection of the detection area without the alteration and possible obscuration of the highlighting.

In another embodiment, the display control will display a frame with multiple detection areas longer. For example, if a frame has N detection areas, the frame could be displayed for about at τ×N time period or, more generally, a period which is a monotonically increasing function of N.

In yet another embodiment, frames with large phase shifts relative to the preceding frame can also be displayed at a slower frame rate to allow the viewer to adjust to the jump in the registration.

According to another embodiment, the total phase shift between two CADe frames could be divided in a nonlinear manner, for example with the rate of phase change maximized midway between the two CADe frames (i.e., accelerating and then decelerating rotation).

In some cases, m may be small and the total phase shift $x_n-x_{n+m}$ large (e.g. the total phase shift greater than a threshold). We can limit the maximum phase shift between any two frames and then relax the requirement that x=0 for the two detection areas, while still keeping the detection areas near the center of the frame.

In yet another embodiment, multiple windows are displayed so that more frames can be displayed simultaneously to reduce the review time. Stacking frames vertically reduces the combined video display aspect ratio to one more comfortable for the reviewer. Two display windows can be used—one for odd-frame video and one for even-frame video. Furthermore, more display windows, such as 4, can be used to accommodate more frames displayed simultaneously. The frame period in this case could be proportional to the sum of the periods calculated for each of those frames that is displayed simultaneously.

Figure 11:
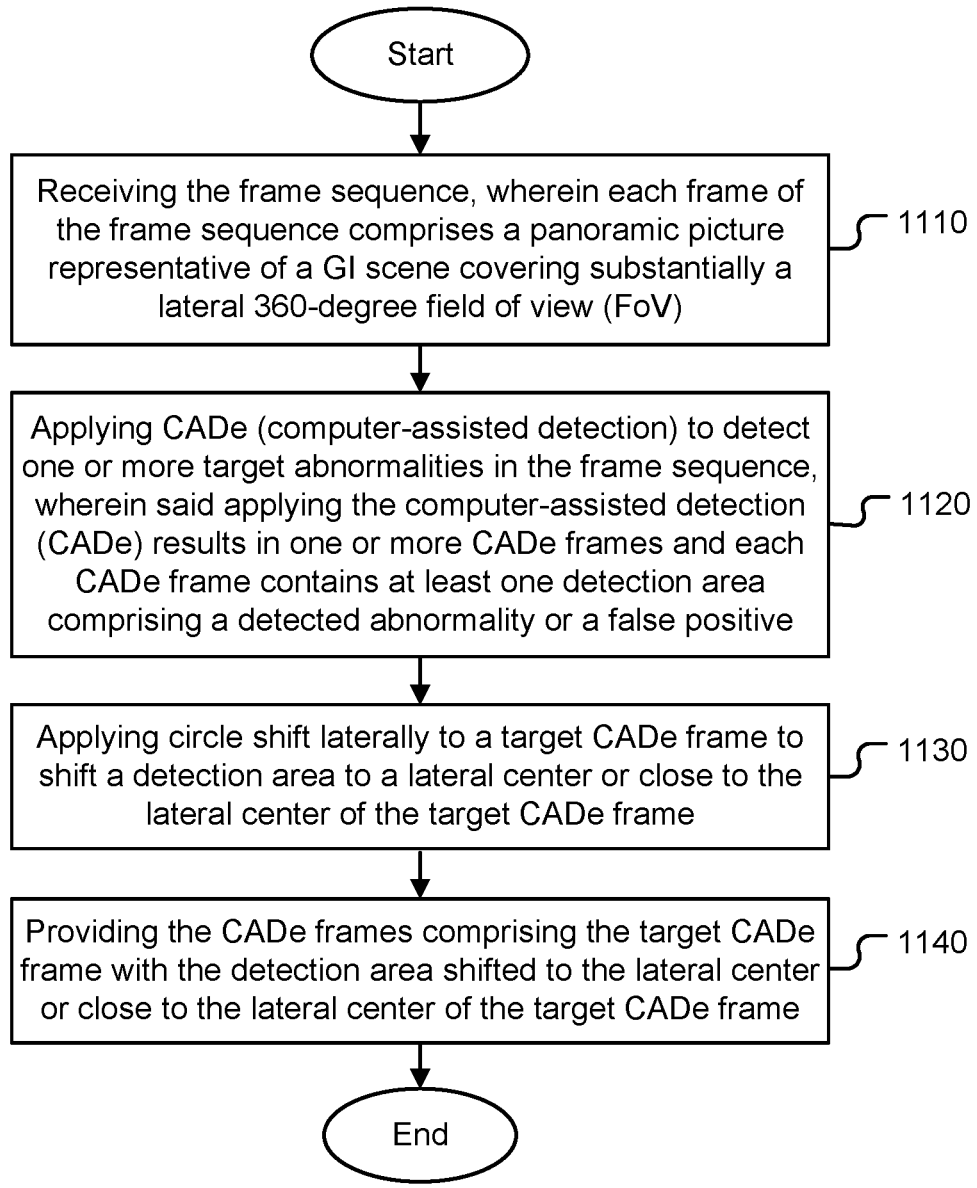
FIG. 11 shows an exemplary flowchart for a method to display a frame sequence corresponding to GI images embodying the present invention.

FIG. 11 shows an exemplary flowchart for a method to process a frame sequence corresponding to GI images embodying the present invention. The steps shown in the flowchart may be implemented as program codes executable on one or more electronic devices or processors (e.g., one or more CPUs). The steps or some of them may be performed on the fly during the video display. For example, the CADe detection may be performed ahead of the viewing time and data designating the detection areas could be encoded in the video file. The circle shifts can be rapidly calculated from the detection area locations and the highlighted applied at the time of the display. Additional adjustments to the video, for example, frame rate adjustment, can either be pre-calculated or calculated and applied during playback.

According to the method, the frame sequence is received in step 1110, wherein each frame of the frame sequence comprises a panoramic picture representative of a GI scene covering substantially a lateral 360-degree Field of view (FoV). CADe (computer-assisted detection) is applied to detect one or more target abnormalities in the frame sequence in step 1120, wherein said applying the computer-assisted detection (CADe) results in one or more CADe frames and each CADe frame contains at least one detection area comprising a detected abnormality or a false positive. Circle shift laterally is applied to a target CADe frame to shift a detection area to a lateral center or close to the lateral center of the target CADe frame in step 1130. The CADe frames comprising the target CADe frame with the detection area shifted to the lateral center or close to the lateral center of the target CADe frame are provided in step 1140.

The invention may be embodied in other specific forms without departing from its spirit or essential characteristics. The described examples are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method for processing a frame sequence corresponding to gastrointestinal (GI) images, the method comprising:
   receiving the frame sequence, wherein each frame of the frame sequence comprises a panoramic picture representative of a GI scene covering substantially a lateral 360-degree field of view (FoV);
   applying CADe (computer-assisted detection) to detect one or more target abnormalities in the frame sequence, wherein said applying CADe to detect said one or more target abnormalities in the frame sequence generates one or more CADe frames and each CADe frame contains at least one detection area comprising a detected abnormality or a false positive, and wherein one or more frames in the frame sequence are skipped for at least one pair of consecutive CADe frames;
   determining horizontal location of said at least one detection area in a target CADe frame;
   in response to the horizontal location of said at least one detection area in the target CADe frame, applying circle shift laterally to the target CADe frame to shift said at least one detection area to a lateral center or close to the lateral center of the target CADe frame; and
   providing the CADe frames comprising the target CADe frame with said at least one detection area shifted to the lateral center or close to the lateral center of the target CADe frame; and
   wherein said applying CADe to detect said one or more target abnormalities in the frame sequence, said determining horizontal location of said at least one detection area and said applying circle shift laterally to the target CADe frame are performed using program codes executable on one or more electronic devices or processors.

2. The method of claim 1, further comprising displaying the CADe frames on a display device.

3. The method of claim 2, wherein the detection area is highlighted.

4. The method of claim 3, wherein the detection area is highlighted using a bounding box.

5. The method of claim 2, wherein when the target CADe frame comprises two or more detection areas, the detection area closest to the lateral center of the CADe frames is highlighted and remaining detection areas are not highlighted.

6. The method of claim 5, wherein at least one additional CADe frame is generated for one of the remaining detection areas and displayed, and wherein said one of the remaining detection areas is highlighted and circularly shifted laterally to near a center of said at least one additional CADe frame and other detection areas are not highlighted.

7. The method of claim 2, wherein for at least two or more closely located detection areas, at least two of said two or more closely located detection areas are highlighted jointly.

8. The method of claim 7, wherein said at least two or more detection areas are highlighted by using a single bounding box to encompass said at least two or more detection areas.

9. The method of claim 2, wherein when one real abnormality appears at least in part in two detection areas at two edges of one target CADe frame prior to the circle shift, the two detection areas are united into one single detection area after the circle shift and said single detection area is highlighted.

10. The method of claim 2, wherein the CADe frames are displayed as a CADe sequence separated from the frame sequence and when one CADe frame displayed in a display window on a display device is selected for further viewing, the display window is switched to display the frame sequence or another display window is used to display the frame sequence.

11. The method of claim 10, wherein after the display window is switched to display the frame sequence or said another display window is used to display the frame sequence, a starting frame of the frame sequence corresponding to the target CADe frame is displayed.

12. The method of claim 11, wherein the starting frame is initially displayed with lateral shifting by a same distance as the target CADe frame.

13. The method of claim 12, wherein the starting frame is displayed without the lateral shifting after a period.

14. The method of claim 10, wherein the detection area is not highlighted after the display window is switched to display the frame sequence.

15. The method of claim 2, wherein when the frame sequence is displayed as a video, intermediate frames between a first target CADe frame and a next target CADe frame are displayed at a slower frame rate if a detection area distance between the first target CADe frame and the next target CADe frame is larger.

16. The method of claim 2, wherein when the frame sequence is displayed as a video and at least one CADe frame with one detection area is displayed for a period t and nearby non-CADe frames in the frame sequence are display for shorter periods.

17. The method of claim 16, wherein when the target CADe frame contains more detection areas, the target CADe frame is displayed for a longer viewing time.

18. The method of claim 2, wherein when the frame sequence is displayed, multiple display windows or a larger display window is used to display multiple frames of the frame sequence simultaneously to reduce viewing time.

19. The method of claim 2, wherein the frame sequence is displayed as a video and the frame sequence comprises intermediate frames without detection areas (non-CADe) between a first target CADe frame shifted by a first shift amount and a second target CADe frame shifted by a second shift amount, the intermediate frames without detection areas are displayed with laterally and circularly shifting in increments corresponding to fractions of a difference between the first shift amount and the second shift amount to avoid large shift between any two frames from the first target CADe frame to the next target CADe frame.

20. The method of claim 19, wherein the increments associated with said laterally and circularly shifting are substantially equal.

21. The method of claim 19, wherein the increments associated with said laterally and circularly shifting increase and then decrease between the first target CADe frame and the second target CADe frame.

22. A system for processing a frame sequence corresponding to gastrointestinal (GI) images, the system comprising:
an interface module coupled to receive the frame sequence, wherein each of the frame sequence comprises a panoramic picture representative of a GI scene covering substantially a lateral 360-degree field of view (FoV);
one or more processing modules coupled to the interface module, wherein said one or more processing modules are configured to:
apply CADe (computer-assisted detection) to detect one or more target abnormalities in the frame sequence, wherein CADe applied to detect said one or more target abnormalities in the frame sequence generates one or more CADe frames and each CADe frame contains at least one detection area comprising a detected abnormality or a false positive, and wherein one or more frames in the frame sequence are skipped for at least one pair of consecutive CADe frames;
determine horizontal location of said at least one detection area in a target CADe frame;
in response to the horizontal location of said at least one detection area in the target CADe frame, apply circle shift laterally to a target CADe frame to shift a detection area to a lateral center or close to the lateral center of the target CADe frame; and
provide the CADe frames comprising the target CADe frame with said at least one detection area shifted to the lateral center or close to the lateral center of the target CADe frame; and
wherein said applying CADe to detect said one or more target abnormalities in the frame sequence, said determining horizontal location of said at least one detection area and said applying circle shift laterally to the target CADe frame are performed using program codes executable on one or more electronic devices or processors.

23. The system of claim 22, further comprising a display device coupled to said one or more processing modules to display the CADe frames comprising the target CADe frame with the detection area shifted to the lateral center or close to the lateral center of the target CADe frame.

* * * * *